US012734220B2

(12) United States Patent
Jorba Ribes et al.

(10) Patent No.: US 12,734,220 B2
(45) Date of Patent: Sep. 15, 2026

(54) COMPOSITION COMPRISING ALBUMIN FOR USE IN THE TREATMENT OF AMYOTROPHIC LATERAL SCLEROSIS (ALS) BY PLASMA EXCHANGE

(71) Applicant: GRIFOLS WORLDWIDE OPERATIONS LIMITED, Dublin (IE)

(72) Inventors: Javier Jorba Ribes, Sant Cugat del Valles (ES); Antonio Manuel Paez Regadera, Sant Cugat del Valles (ES)

(73) Assignee: GRIFOLS WORLDWIDE OPERATIONS LIMITED, Dublin (IE)

( * ) Notice: Subject to any disclaimer, the term of this patent is extended or adjusted under 35 U.S.C. 154(b) by 867 days.

(21) Appl. No.: 17/997,730

(22) PCT Filed: Apr. 27, 2021

(86) PCT No.: PCT/EP2021/060920
§ 371 (c)(1),
(2) Date: Nov. 1, 2022

(87) PCT Pub. No.: WO2021/224058
PCT Pub. Date: Nov. 11, 2021

(65) Prior Publication Data

US 2023/0158120 A1 May 25, 2023

(30) Foreign Application Priority Data

May 7, 2020 (EP) .................................... 20382375

(51) Int. Cl.
*A61K 38/38* (2006.01)
*A61P 25/28* (2006.01)

(52) U.S. Cl.
CPC ............ *A61K 38/385* (2013.01); *A61P 25/28* (2018.01)

(58) Field of Classification Search
None
See application file for complete search history.

(56) References Cited

FOREIGN PATENT DOCUMENTS

| | | |
|---|---|---|
| ES | 2 535 579 A1 | 5/2015 |
| WO | WO 2014/159247 | 10/2014 |
| WO | WO 2020/018343 A1 | 1/2020 |

OTHER PUBLICATIONS

Kelemen et al., "Plasmapheresis with immunosuppression in Amyotrophic Lateral Sclerosis", Arch Neurol. vol. 40, No. 12, pp. 752-753 (Year: 1983).*

Instituto Grifols, et al.: "Study details tabular view study results disclaimer how to read a study record efficacy and safety of plasma exchange with albumin in patients with amyotrophic lateral sclerosis sponsor: study description amyotrophic lateral sclerosis biological: albumin phase 2 go to", Jun. 24, 2015, xp055738310, retrieved from the internet: url:https://clinicaltrials.gov/ct2/show/nct02479802.

Chio, et al: "Amyotrophic lateral sclerosis outcome measures and the role of albumin and creatinine: a population-based study", JAMA Neurology, vol. 71, No. 9, Sep. 1, 2014.

Silani, et al., "Plasma Exchange Ineffective in Amyotrophic Lateral Sclerosis" Arch. Neurol. (1980) vol. 37: 511-513.

Kelemen, et al., T.L. "Plasmapheresis with immunosupression in Amyotrophic Lateral Sclerosis". Arch. Neurol. (1983), vol. 40: 752-753.

Schwartz, et al., "Guidelines on the use of therapeutic apheresis in clinical practice-evidence-based approach from the Writing Committee of the American Society for Apheresis: the sixth special issue" J. Clin. Apher. Jul. 2013; 28(3):145-284.

Notice of Reasons for Refusal issued Jan. 7, 2025, in Japanese Patent Application No. 2022-566698 which corresponds to the present application.

ClinicalTrials.gov archive: NCT02872142, [Dec. 17, 2024 search, 2020 years, 03 months, 11 days, https://clinicaltrials.gov/study/NCT02872142.

* cited by examiner

*Primary Examiner* — Anand U Desai
(74) *Attorney, Agent, or Firm* — Knobbe, Martens, Olson & Bear LLP

(57) ABSTRACT

A composition including albumin for use in the treatment of Amyotrophic Lateral Sclerosis (ALS), wherein the composition is administrated to the patient by plasma exchange using a volume of the composition equivalent to approximately 100% of the volume of plasma withdrawn from the patient, and with a frequency of twice a week the first 3 weeks and once a week for the following 21 weeks, for a total period of 24 weeks.

3 Claims, No Drawings

COMPOSITION COMPRISING ALBUMIN FOR USE IN THE TREATMENT OF AMYOTROPHIC LATERAL SCLEROSIS (ALS) BY PLASMA EXCHANGE

PRIORITY AND CROSS REFERENCE TO RELATED APPLICATIONS

This application is the U.S. National Phase Application under 35 U.S.C. § 371 of International Application No. PCT/EP2021/060920, filed Apr. 27, 2021, designating the U.S. and published as WO 2021/224058A1 on Nov. 11, 2021, which claims the benefit of European Application No. 20382375.2, filed May 7, 2020. Any and all applications for which a foreign or a domestic priority is claimed is/are identified in the Application Data Sheet filed herewith and is/are hereby incorporated by reference in their entireties under 37 C.F.R. § 1.57.

FIELD

The present invention relates to a composition comprising albumin for use in the treatment of amyotrophic lateral sclerosis (ALS) by plasma exchange.

BACKGROUND

Amyotrophic lateral sclerosis (ALS) is a motor neurone disease affecting about 3 of 100.000 people a year in United States. ALS is a chronic, progressive and fatal degenerative neurological disease that causes the death of motor neurons controlling voluntary muscles. For 90% of cases, the origin of the disease is unknown and sporadic. Despite extensive studies on this disease, its pathogenesis has not been identified yet and no effective treatment has been found.

As previously mentioned, ALS is usually progressive, with upper and lower motor paralysis leading to an average survival of three years from the start of the disease. In general, difficult and distressing medical problems arise during the course of the disease, which have motivated the use of a wide variety of treatments, such as toxic drugs, inactivated cobra venom and plasmapheresis, among others.

Plasmapheresis is a common medical procedure in which plasma from a patient is separated from whole blood. It has been used to treat patients suffering from different chronic diseases. Once the plasma is separated from the blood cells, the cells can be returned to the patient with or without replacement fluids. During treatment of patients by therapeutic plasmapheresis, a catheter is placed in a major vein, for example in the arm, and a second catheter is placed in another vein, for example, in the foot or hand. The blood then leaves the patient's body through the catheter and is sent to a separating device, where the plasma is separated from the blood cells. Blood without plasma and, optionally, along with replacement fluid, is returned to the patient through the second catheter. Instead of two peripheral catheters, a dual-channel, central, or peripheral catheter can also be used.

The use of plasmapheresis for the treatment of ALS has been previously reported. For example, Silani et al. used plasma exchange with frozen plasma and saline for the treatment of four ALS patients during six months (Silani, V., Scarlato, G., Valli, G. and Marconi, M. "Plasma Exchange Ineffective in Amyotrophic Lateral Sclerosis" Arch. Neurol. (1980) Vol. 37: 511-513). However said treatment was unsuccessful and did not change the course of the disease. In addition, in a later work of Kelemen et al., the use of plasma exchange with albumin at 5% in combination with immunosuppressants for the treatment of ALS shown no beneficial effect on the disease, nor any clinical improvement in any of the 4 patients studied (Kelemen, J., Hedlund, W., Orlin, J. B., Berkman, E. M. and Munsat T. L. "Plasmapheresis with immunosupression in Amyotrophic Lateral Sclerosis". Arch. Neurol. (1983), Vol. 40: 752-753.).

These previous works explain why the use of plasma exchange in the treatment of ALS is considered of category IV (the lower) in the guidelines on the use of therapeutic apheresis in clinical practice by the American Society for Apheresis (Schwartz, J., Winters, J. L., Padmanabhan, A., Balogun, R. A., Delaney, M., Linenberger, M. L., Szczepiorkowski, Z. M., Williams, M. E., Wu, Y., Shaz B. H. "Guidelines on the use of therapeutic apheresis in clinical practice-evidence-based approach from the Writing Committee of the American Society for Apheresis: the sixth special issue" J. Clin. Apher. 2013 July; 28(3):145-284). Category IV relates to disorders in which published evidence demonstrates or suggests apheresis to be ineffective or harmful.

More recently, it was shown in the Spanish Patent ES201530074 that the use of a composition comprising albumin for the treatment of ALS by plasma exchange could provide some beneficial effects on the course of the disease. In said Spanish Patent, an ALS patient was treated during 14 weeks with a composition comprising human albumin at 5% (w/v) by plasma exchange 3 times a week during the 2 first weeks and once a week during the other 12 weeks. The effect of said specific treatment was evaluated using a functional qualification of ALS from a period starting 12 months prior the treatment and finalizing 2 months after the end of the treatment. The results of said functional qualification showed a tendency to stabilization of the course of the disease over time, which was unexpected since it is well known that a ALS patient's condition always tends to worsen.

However, said study was conducted with only one patient for whom the course of the disease was maintained, but not improved in any way.

Therefore, there remains a need for a treatment of ALS by plasma exchange that could avoid the normal progression of the disease and could even improve the functional qualification of the patient.

SUMMARY

In some embodiments, a composition includes albumin for use in the treatment of Amyotrophic Lateral Sclerosis (ALS) in a patient in need thereof, wherein the composition is administrated to said the patient by plasma exchange using a volume of said the composition equivalent to approximately 100% of the volume of plasma withdrawn from the patient, and with a frequency of twice a week the first 3 weeks and once a week for the following 21 weeks, for a total period of 24 weeks.

In some embodiment, the method for treating Amyotrophic Lateral Sclerosis (ALS) in a patient in need thereof, comprising the administration of a composition comprising of albumin by plasma exchange using a volume of said composition equivalent to approximately 100% of the volume of plasma withdrawn from the patient, and with a frequency of twice a week the first 3 weeks and once a week for the following 21 weeks, for a total period of 24 weeks.

In some embodiment, the concentration of albumin in the composition is between 5% and 25% (w/v). In some embodiment, the concentration of albumin in the composition is about 5% (w/v). In some embodiment, the concentration of albumin is recombinant or purified from human plasma. In some embodiment, the use of immunosuppressants is not required.

DETAILED DESCRIPTION

The inventors of the present invention have surprisingly found that the use of a composition comprising albumin for the treatment of ALS by plasma exchange could indeed improve the progression of the disease by using specific treatment conditions.

Therefore, in a first aspect the present invention relates to a composition comprising albumin for use in the treatment of ALS by plasma exchange.

Preferably, the albumin concentration in said composition is between 5% and 25% (w/v). More preferably, the concentration of albumin is about 5%, 10%, 15%, 20% or 25% (w/v). Even more preferably, the concentration of albumin is about 5% (w/v).

Albumin can be either recombinant or purified from human plasma. In a preferred embodiment, the albumin is purified from human plasma.

In preferred embodiments of the present invention, the composition comprising albumin for use in the treatment of ALS is administrated to a patient in need thereof by plasma exchange using a volume of said composition equivalent to approximately 100% of the volume of plasma withdrawn from the patient. In preferred embodiments, said composition is administrated to the patient by plasma exchange twice a week the first 3 weeks and once a week for the following 21 weeks, for a total period of 24 weeks.

In the present invention, treatment with the composition comprising albumin is preferably carried out by plasma exchange, i.e. said composition comprising albumin is used as replacement liquid and will be returned to the patient along with the blood cells, which have been previously separated from the plasma by plasmapheresis. In general, a determined volume of plasma is withdrawn from the patient and the plasma exchange with the composition comprising albumin is carried out with a volume of said composition equivalent to approximately 100% of the volume of plasma withdrawn from the patient. A person skilled in the art understands that small variations of approximately ±10% of this volume will fall within the scope of the present invention.

One of the main difference from the use of a composition comprising albumin for the treatment of ALS according to the present invention and the treatments known in the prior art, is that in the present treatment the use of immunosuppressants is not necessary before, during or after finishing said treatment. ALS has been linked in the prior art to abnormalities of the immune system such as abnormalities of surface antigens, T lymphocytes, and macrophage migration (Kelemen J. et al., Above), which may suggest the use of a concomitantly immunosuppressant treatment with any ALS treatment. However, it is demonstrated herein that the use of immunosuppressants is not necessary with the treatment of the present invention to obtain satisfactory results for the treatment of ALS. Thus, in some embodiments, the use of immunosuppressants is not required during the treatment with the composition of the present invention. However, in other embodiments, the use immunosuppressants during the treatment of ALS with the composition of the present invention is also possible if required by other conditions of the patient.

In the treatment of the present invention, the plasma exchange using the composition comprising albumin as replacement fluid is carried out with a frequency of twice a week the first 3 weeks and once a week during the following 21 weeks, which correspond to a total period of 24 weeks.

During the duration of the treatment according to the present invention, patients may experience, at least, a tendency to stabilize the course of the disease. In other words, since ALS is a disease whose progression is rapid and gradual once ALS symptoms onset, achieving stabilization of its progression during the duration of the treatment can be considered a very positive result. In addition to that, the treatment of the present invention has also demonstrated to improve the functional qualification of some of the patients and therefore, to reverse the progression of the disease to less advanced stages.

In a second aspect, the present invention relates to a method for treating ALS in a patient in need thereof, comprising the administration of a composition comprising albumin by plasma exchange. Preferably, said plasma exchange is carried out using a volume of said composition equivalent to approximately 100% of the volume of plasma extracted from the patient. A person skilled in the art understands that small variations of approximately ±10% of this volume will fall within the scope of the present invention. In some preferred embodiments, said method for treating ALS is carried out with a frequency of twice a week the first 3 weeks and once a week during the following 21 weeks, for a total period of 24 weeks.

Preferably, the albumin concentration in said composition is between 5% and 25% (w/v). More preferably, the concentration of albumin is about 5%, 10%, 15%, 20% or 25% (w/v). Even more preferably, the concentration of albumin is about 5% (w/v).

Albumin can be either recombinant or purified from human plasma. In a preferred embodiment, the albumin is purified from human plasma.

In some embodiments, the use of immunosuppressants is not required during the method for treating ALS of the present invention.

Hereinafter, the present invention is described in more detail with reference to illustrative examples, which does not constitute a limitation of the present invention.

EXAMPLE

Plasma exchange (PE) with albumin 5% (Albutein®, Grifols, S. A., Spain) in patients diagnosed with ALS.

Men and women aged 18 to <70 years with a definite, possible or probable diagnosis of ALS according to El Escorial/Airlie House criteria, and having a forced vital capacity (FVC)>70% of predicted value were eligible for a prospective, single-arm, single-center, pilot study.

Patients underwent 6-month of PE-treatment using 5% albumin (Albutein® 5%) in 2 phases: one intensive phase involving 2 PE sessions per week for 3 weeks, followed by a maintenance phase involving one PE session per week for 21 weeks. The follow-up period was 6-month.

Endpoints were changes in Revised Amyotrophic Lateral Sclerosis Functional Rating Scale (ALSFRS-R) score and FVC. Based on the typical survival of 3-5 years from time of ALS symptoms onset, and the typical decrease of 1 point/month in the ALSFRS-R overall score, three categories of disease progression were defined: "normal", "slow", and "fast", depending on whether ALSFRS-R slope was between −0.8 and −1.33 points/month, <−0.8 points/month, or >−1.33 points/month, respectively.

Thirteen adults with ALS were enrolled and evaluated. Median (IQR) overall score at baseline was 42.0 (37.0, 44.0). ALSFRS-R score declined throughout the study, although the median decline was less than expected in untreated patients. Seven patients at the end of treatment and 5 patients at the end of study had a slower decline than expected. Six patients remained in the same "progressor" category while 4 improved their category at the end of the treatment. Median (IQR) of FVC and predicted FVC percentage at baseline were 3.9 (3.0, 4.9) L and 87.0% (76.0, 96.0), respectively. Median FVC decreased significantly during the study. The treatment was well tolerated.

Plasma Exchange with albumin replacement was safe and well tolerated in ALS patients. Although functional impairment progressed, most patients showed a slower than expected rate of decline at the end of treatment. In terms of slope progression most patients either remained stable (54.5%) or improved (36.4%) their category.

Thus, the treatment of the present invention has been proved not only to stabilize the course of the disease but also to improve the conditions of the patients and therefore, to reverse the progression of the disease to less advanced stages.

Although the invention has been described with respect to a preferred embodiment, this should not be considered as limiting the invention, which will be defined by the broadest interpretation of the following claims.

What is claimed is:

1. A method for treating Amyotrophic Lateral Sclerosis (ALS) in a patient, comprising: administering a composition comprising albumin by plasma exchange using a volume of said composition equivalent to 100%±10% of the volume of plasma withdrawn from the patient, and with a frequency of twice a week the first 3 weeks and once a week for the following 21 weeks, for a total of 24 weeks, wherein the concentration of albumin in the composition is 5% (w/v).

2. The method according to claim 1, wherein the albumin is recombinant or purified from human plasma.

3. The method according to claim 1, wherein immunosuppressants are not required.

* * * * *